(12) United States Patent
Jacquot

(10) Patent No.: US 6,180,830 B1
(45) Date of Patent: *Jan. 30, 2001

(54) METHOD FOR PREPARING A BIMETALLIC RUTHENIUM/TIN CATALYST AND A PROCESS FOR THE SYNTHESIS OF ALDEHYDES

(75) Inventor: Roland Jacquot, Sainte-Foy-les-Lyon (FR)

(73) Assignee: Rhodia Chimie, Courbevoie (FR)

( * ) Notice: Under 35 U.S.C. 154(b), the term of this patent shall be extended for 0 days.

This patent is subject to a terminal disclaimer.

(21) Appl. No.: 09/068,263

(22) PCT Filed: Nov. 8, 1996

(86) PCT No.: PCT/FR96/01762

§ 371 Date: May 5, 1998

§ 102(e) Date: May 5, 1998

(87) PCT Pub. No.: WO97/17135

PCT Pub. Date: May 15, 1997

(30) Foreign Application Priority Data

Nov. 8, 1995 (FR) .................................................. 96 13185

(51) Int. Cl.$^7$ .......................... C07C 47/27; B01J 27/135; B01J 23/40

(52) U.S. Cl. ......................... 568/435; 568/484; 502/227; 502/230; 502/326; 502/261; 502/349; 502/352

(58) Field of Search .................................... 568/435, 426, 568/449, 486; 502/227, 230, 332, 349, 352, 326, 261

(56) References Cited

U.S. PATENT DOCUMENTS

| 4,117,082 | | 9/1978 | Matsuyama | 423/247 |
|---|---|---|---|---|
| 4,218,401 | | 8/1980 | Wymore | 567/402 |
| 4,490,482 | | 12/1984 | Mathieu | 502/339 |
| 5,334,769 | * | 8/1994 | Ferrero et al. | 568/435 |
| 5,973,210 | | 10/1999 | Jacquot | 568/484 |

FOREIGN PATENT DOCUMENTS

| 0 539 274 | 4/1993 | (EP) | C07C/45/41 |
|---|---|---|---|
| 0 626 201 | 11/1994 | (EP) | B01J/31/16 |
| WO 93/14866 | 8/1993 | (WO) | B01J/23/62 |
| WO/96/22832 | 8/1996 | (WO) | B01J/23/62 |

* cited by examiner

Primary Examiner—Sreeni Padmanabhan
(74) Attorney, Agent, or Firm—Jean-Louis Seugnet

(57) ABSTRACT

The present invention relates to a new process for the preparation of a bimetallic ruthenium/tin catalyst. The process for the preparation of a bimetallic ruthenium/tin catalyst according to the invention is characterised by the fact that it consists in carrying out the reduction of a ruthenium complex having an electrovalency of −4 and a coordination number of 6, the ligands being either a halogen atom or an anion or a tin halide. The catalyst is further employed for the preparation of aldehydes by reduction, in the vapor phase, of carboxylic acids, esters and anhydrides.

40 Claims, No Drawings

METHOD FOR PREPARING A BIMETALLIC RUTHENIUM/TIN CATALYST AND A PROCESS FOR THE SYNTHESIS OF ALDEHYDES

This application is an application under 35 U.S.C. Section 371 of International Application Number PCT/FR96/01762, filed on Nov. 08, 1996.

The present invention relates to a new process for the preparation of a bimetallic ruthenium/tin catalyst.

EP-A-0 539 274 described a process for the preparation of aldehydes and derivatives thereof according to a process which consists in carrying out the reduction, in the vapour phase in the presence of hydrogen, of carboxylic acids, esters or anhydrides, in the presence of a bimetallic ruthenium/tin catalyst.

Although catalysts of the ruthenium/tin type containing boron are suitable for performing the process described, the catalysts of particular interest are boron-free bimetallic catalysts containing tin and ruthenium, which contain ruthenium and tin used in such quantities that the molar ratio of tin/ruthenium is at least 2, preferably between 2 and 10 inclusive and even more preferably between 2 and 6 inclusive.

It is possible to use different types of catalysts which may or may not be supported.

Generally speaking, ruthenium represents between 0.1 and 50% of the weight of the catalyst.

If a solid catalyst is used, the ruthenium represents 10% to 50% of the weight of the catalyst.

In a preferred embodiment, however, a catalyst in the supported form is used. To this end, the support may be chosen in particular from metal oxides such as aluminium, silicon and/or zirconium oxides, or from carbons optionally activated by a well known treatment with nitric acid, acetylene black, or resins.

If the catalytic phase is deposited on a support, the ruthenium content of the catalyst is advantageously between 0.1 and 20.0% by weight, and even more preferably between 0.5 and 3.0% by weight.

A method of preparing said catalysts described in EP-A-0 539 274 consists in mixing ruthenium III chloride and tin II chloride then adding the solid support.

The disadvantage of this process is that it does not make it possible to obtain a perfectly homogeneous catalyst that can be produced on an industrial scale. Indeed, tin II chloride partially hydrolyses and precipitates on the surface of the support whereas ruthenium III chloride penetrates the pores of the support. As a result, the support is not impregnated uniformly by the precursors of the ruthenium and tin metals and the catalyst obtained is not very homogeneous.

The object of the present invention is to provide a process for the preparation of said catalyst which makes it possible to overcome the above-mentioned disadvantages.

A process has now been found, and this constitutes the subject matter of the present invention, for the preparation of a bimetallic ruthenium/tin catalyst, characterised in that it consists in carrying out the reduction of a ruthenium complex having an electrovalency of −4 and a coordination number of 6, the ligands being either a halogen atom or an anion of tin halide.

According to a preferred embodiment of the process of the invention, the reduction of a complex corresponding more particularly to the following formula (A) is carried out:

$$[Ru(SnX_3)_{6-n}X_n]^{4-} \quad (A)$$

in which formula (A) X represents a halogen atom, preferably an atom of chlorine or bromine, and n is a number ranging from 0 to 2, and preferably equal to 1.

In the process of the invention, the following complexes are used in preference:

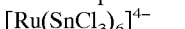
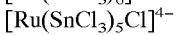

$[Ru(SnCl_3)_6]^{4-}$
$[Ru(SnCl_3)_5Cl]^{4-}$
$[Ru(SnCl_3)_4Cl_2]^{4-}$

It was found that the catalyst obtained was of good quality if it was prepared according to the process of the invention as specified.

A halogenated complex of ruthenium and tin corresponding preferably to formula (A) is therefore used in the process of the invention.

According to a preferred embodiment of the invention, the preparation of said complex is carried out by reaction of a ruthenium halide and of a tin halide in the presence of an acid.

To this end, the starting product is a ruthenium III halide, preferably a ruthenium III chloride. It is also possible to start with a ruthenium IV salt, but there is no additional advantage, particularly as it is more expensive.

In preference, therefore, a ruthenium III halide, either in the anhydrous or hydrated form, is used.

It is desirable that said compound does not contain too many impurities. Advantageously, the compound used is free from heavy metals and has a chemical ruthenium purity of 99% with respect to the other metals.

It is possible to use the commercial form of ruthenium chloride $RuCl_3 \times H_2O$ containing about 42 to 43% by weight of ruthenium without any disadvantages.

With regard to the tin salt, a tin halide is used in which the tin has an oxidation number lower than that of the ruthenium.

A tin II halide is used, preferably a tin II chloride.

It is also possible to use the salt in the anhydrous or hydrated form. In preference, the commercial tin salt having the formula $SnCl_2 \cdot 2H_2O$ is also used.

Most often, the halides of said metals are used in the form of an aqueous solution. The concentration of these solutions is such that a homogeneous solution capable of being impregnated on a support is obtained.

With regard to the quantities of the above-mentioned metal halides used, said quantity is determined in such a way that the ratio between the number of moles of ruthenium halide and the number of moles of tin halide is between 0.10 and 0.5, and preferably between 0.15 and 0.35. It should be noted that the lower limit is not critical because there is no disadvantage in using an excess of tin halide.

The preparation of the complex by reaction of the ruthenium and tin halides takes place in the presence of an acid, the function of which is to solubilise the tin halide and to keep the complex formed soluble.

It is possible to use any strong, preferably mineral acid, but it is preferable to use the hydracid of which the halide is identical to the halide used in the ruthenium and tin salts.

Thus, hydrochloric acid is generally the preferred acid.

The quantity of acid used is preferably at least 1 mole of acid per mole of ruthenium halide, and more particularly between 1 and 5 moles of acid per mole of ruthenium halide. The upper limit is not critical and may be exceeded without disadvantage. The preferred quantity of acid is in the region of 3 moles of acid per mole of ruthenium halide.

From a practical point of view, the preparation of the complex is carried out by mixing, in any order, the ruthenium halide (preferably ruthenium III chloride), the tin halide (preferably tin II chloride) and the strong acid (preferably hydrochloric acid).

The reaction mixture is brought to a temperature from 20° C. to 100° C., preferably between 70° C. and 90° C.

The duration of this operation may vary widely and it may be specified by way of illustration that a period between 1 and 3 hours is perfectly suitable.

The complex forms fairly rapidly but it remains in solution.

Afterwards, if necessary, the temperature is restored to ambient temperature, that is, to a temperature most open between 15° C. and 25° C.

It is thus possible to envisage two variants of the process depending on whether the desire is to obtain a catalyst in the solid or supported form.

In the first case, hydrolysis of the complex obtained is carried out by adding water.

The amount of water used is not critical; it generally represents 1 to 100 times the weight of the complex.

After this hydrolysis, the complex precipitates.

It may be separated by conventional solid/liquid separation techniques, preferably by filtration.

This separation is generally carried out at ambient temperature.

The precipitate obtained may optionally be dried then reduced according to the conditions defined below.

If the support is in the form of a powder, such as, for example, alumina or silica, another variant consists in adding it to the solution of the complex obtained, then carrying out hydrolysis as described above, then separating the solid obtained, preferably by filtration, and mixing it and extruding it. A formed catalyst is thus obtained.

According to another preferred variant of the process of the invention, the solution of the complex obtained previously is used to impregnate a support.

The support may take any form, for example, a powder, beads, granules, extrudates, etc.

With regard to the nature of the support, examples of support are given above such as metal oxides, such as aluminium, silicon and/or zirconium oxides, or active carbons, or resins.

In the case of a supported catalyst, the ruthenium content is adapted by the man skilled in the art according to the support (nature, specific surface).

Generally speaking, the ruthenium content of the catalyst is advantageously between 0.1 and 20.0% by weight, and even more preferably between 0.5 and 3.0% by weight.

From a practical point of view, the metals are deposited on the support by impregnating said support with the solution of the complex obtained according to the process described above.

The aqueous impregnation solution contains the ruthenium and tin complex in a quantity of 1% to 20% by weight of ruthenium.

In a practical manner, impregnation may be carried out by spraying the solution containing the ruthenium and tin complex onto the support brought into motion, for example, by the rotation of a rotatable outer ring.

It is also possible to start with a support resulting from an agglomeration of its particles according to well known methods, for example, of extrusion or pelletising by pressure, then to impregnate the support by immersing it in the solution of said complex.

According to a preferred variant of the invention, impregnation is carried out "in the dry state", that is the total volume of the solution of complex used is approximately equal to the pore volume presented by the support. The pore volume may be determined by any known method, particularly according to the mercury porosimeter method (ASTM D 4284-83) or by measuring the quantity of water that a sample will absorb In the next stage, the impregnated support or the separated precipitate obtained according to the first variant then undergoes a reduction operation.

A preferred variant of the invention consists in carrying out a drying stage beforehand.

Drying is most often carried out in the air at a temperature which may range from ambient temperature, for example 20° C. to 100° C.

The drying period is continued until a constant weight is obtained.

Generally speaking, it ranges from 1 to 24 hours, depending on the temperature chosen.

In the next stage, the complex is reduced by bringing the solid or supported catalyst into contact with the reducing agent.

It is possible to envisage a chemical reducing agent but this has no specific advantage. Thus, reduction is carried out preferably with hydrogen.

Hydrogen may be injected at atmospheric pressure or under a slight pressure, for example 0.5 to 10 bar, preferably between 1 and 2 bar.

The hydrogen may also be diluted in an inert gas such as nitrogen or helium

Advantageously, the reduction reaction is carried out at a temperature of at least 350° C., preferably between 350° C. and 600° C., and even more preferably between 400 and 500° C.

It is understood that reduction may also be carried out during the use of the catalyst if it is used in a reduction reaction of a substrate in the presence of hydrogen.

Thus, in the process for the preparation of aldehydes and derivatives thereof described in EP-A-0 539 274 according to a process which involves carrying out the reduction, in the vapour phase in the presence of hydrogen, of carboxylic acids, esters or anhydrides in the presence of a bimetallic ruthenium/tin catalyst, said catalyst may be prepared at the start of the reaction, by reduction of a ruthenium and tin complex as defined by the invention.

The supported catalyst of the ruthenium/tin type thus obtained is particularly homogeneous and may easily be prepared on an industrial scale.

It contains a metallic phase covering at least in part said support containing at least in part a ruthenium/tin intermetallic phase at least partially in the form of the defined compound of $Ru_3Sn_7$.

Advantageously, the phase containing the ruthenium and tin has an atomic ratio of Sn/Ru at least equal to 2/3, advantageously 3/2, preferably 7/3.

Moreover, it is preferable that the atomic ratio Sn/Ru be at most equal to 3, advantageously 5/2.

In the preferred catalysts, the said phase covering at least in part said support contains at least 50% advantageously 80%, preferably at least 90% of said intermetallic phase.

Finally, it is desirable that at least 90%, advantageously at least 95%, preferably 98% of the ruthenium present on the support be in the form of said phase covering said support.

It is very advantageous to use the catalyst obtained according to the invention in the process for the preparation of aldehydes and derivatives described in EP-A-0 539 274 which is incorporated by reference in the present application.

Indeed, it may be used advantageously to carry out the reduction, by hydrogen, of carboxylic acids, esters or anhydrides in the vapour phase.

More particularly, the catalyst is well suited to the preparation of aldehydes having the general formula:

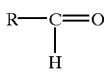
(I)

in which R represents a hydrogen atom or an optionally substituted hydrocarbon radical containing 1 to 40 carbon atoms which may be a saturated or unsaturated, linear or branched, acyclic aliphatic radical; a saturated, unsaturated or aromatic, monocyclic or polycyclic, carbocyclic or heterocyclic radical, by reduction of esters, anhydrides or acids having the formula:

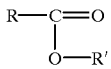
(II)

in which:

R is defined as above,

R' represents:
  an R group as defined above,
  an

R″—C=O group in which R″ has the meaning given for R, group in which R″ has the meaning given for R,
  the two groups R and R″ may be linked to form a saturated or unsaturated ring having 5 to 7 atoms and containing the anhydride function,
  the two groups R and R″, by way of two vicinal atoms, may together form a bridge of an ortho-condensed bicyclic system.

In accordance with the process of the invention, it is possible to use any carboxylic acid capable of being in the gaseous form under the conditions of the invention.

The process of the invention applies to any mono- or polycarboxylic acid such as saturated or unsaturated aliphatic acids; saturated, unsaturated or aromatic, monocyclic or polycyclic, carbocyclic or heterocyclic acids; saturated or unsaturated aliphatic acids bearing a cyclic substituent such as a saturated, unsaturated or aromatic, carbocyclic or heterocyclic ring.

The starting raw material used may thus be a carboxylic acid corresponding to formula (II) in which the radical R represents a substituted or unsubstituted hydrocarbon radical which may be a linear or branched, saturated or unsaturated acyclic aliphatic radical; a saturated, unsaturated or aromatic, monocyclic or polycyclic, carbocyclic or heterocyclic radical.

The carboxylic acids or derivatives used in preference correspond to formula (II) in which R represents an optionally substituted hydrocarbon radical containing 1 to 20 carbon atoms.

The carboxylic acids that are particularly suitable for performing the process of the invention have the general formula (II) in which R represents an optionally substituted, monocyclic or polycyclic aromatic hydrocarbon radical.

Any substituent may be present on the ring provided that it does not interfere with the reduction reaction of the carboxylic function.

R preferably represents an aromatic hydrocarbon radical, and particularly a benzene ring, corresponding to the general formula (III):

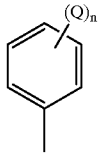
(III)

in which formula (III)

n is an integer from 0 to 5, preferably 0 to 3;

Q represents $R_1$, one of the following groups or functions:
  a linear or branched alkyl radical having 1 to 6 carbon atoms, preferably 1 to 4 carbon atoms, such as methyl, ethyl, propyl, isopropyl, butyl, isobutyl, sec-butyl, tert-butyl,
  a linear or branched alkenyl radical having 2 to 6 carbon atoms, preferably 2 to 4 carbon atoms, such as vinyl, allyl,
  a linear or branched alkoxy radical having 1 to 6 carbon atoms, preferably 1 to 4 carbon atoms such as methoxy, ethoxy, propoxy, isopropoxy, butoxy radicals,
  an acyl group having 2 to 6 carbon atoms,
  a radical having the formula:
    —$R_2$—OH
    —$R_2$—COO$R_5$
    —$R_2$—CHO
    —$R_2$—NO$_2$
    —$R_2$—CN
    —$R_2$—N($R_5$)$_2$
    —$R_2$—CO—N($R_5$)$_2$
    —$R_2$—SH
    —$R_2$—X
    —$R_2$—CF$_3$
    in which formulae $R_2$ represents a valency bond or a saturated or unsaturated, linear or branched, divalent hydrocarbon radical having 1 to 6 carbon atoms such as, for example, methylene, ethylene, propylene, isopropylene, isopropylidene; the radicals $R_5$, which may be the same or different, represent a hydrogen atom or a linear or branched alkyl radical having 1 to 6 carbon atoms; X symbolises a halogen atom, preferably an atom of chlorine, bromine or fluorine.

Q represents $R_3$, one of the following more complex radicals:
  a radical

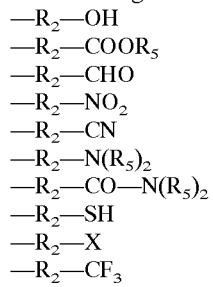

in which $R_1$ and $R_2$ have the meaning given above and m is an integer from 0 to 5, preferably 0 to 3,
  a radical $R_2.A.R_4$ in which $R_2$ has the meaning given above, $R_4$ represents a linear or branched alkyl radical having 1 to 6 carbon atoms, preferably 1 to 4 carbon atoms, or a radical having the formula

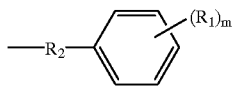

and A symbolises one of the following groups:

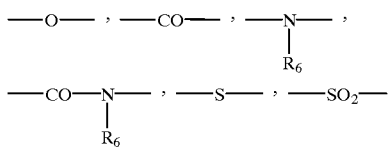

in these formulae $R_6$ represents a hydrogen atom or a linear or branched alkyl radical having 1 to 4 carbon atoms, preferably a methyl or ethyl radical.

If n is greater than 1, the radicals Q may be the same or different and 2 successive carbon atoms of the benzene ring may be linked together by a ketal bridge such as the methylenedioxy or extranuclear ethylenedioxy radicals.

Preferably, n is equal to 0, 1, 2 or 3.

Of all the above-mentioned R radicals it is preferable to use in the process of the invention the carboxylic acids or derivatives corresponding to the general formula (II) in which R represents an aromatic radical corresponding to the general formula (III) in which:

n is equal to 0, 1, 2 or 3,

Q represents one of the following groups or functions:
  a hydrogen atom,
  a linear or branched alkyl radical having 1 to 4 carbon atoms,
  a linear or branched alkoxy radical having 1 to 4 carbon atoms,
  a methylenedioxy or ethylenedioxy radical,
  an —OH group,
  a —CHO group,
  an $NH_2$ group,
  a phenyl radical,
  a halogen atom,
  a $CF_3$ group.

Even more preferably, the compounds chosen correspond to formula (II) in which the radicals Q, which may be the same or different, are a hydrogen atom, a hydroxyl group, a methyl radical, a methoxy radical, a —CHO group.

Examples of radicals R which correspond to the formula (III) include, more particularly, the phenyl, tolyl or xylyl radicals and the biphenyl, methylene-1,1'biphenyl, isopropylidene-1,1'biphenyl, oxy-1,1'biphenyl, imino-1,1'biphenyl radicals; said radicals may be substituted by one or more Q radicals as defined above, preferably a hydroxyl group or a halogen atom.

R may also represent a polycyclic aromatic hydrocarbon radical; the rings may form ortho-condensed, ortho- and peri-condensed systems. The following may be mentioned more particularly: a naphthalene radical; said rings may be substituted by 1 to 4 $R_1$ radicals, preferably 1 to 3, $R_1$ having the meanings given above for the substituents of the aromatic hydrocarbon radical corresponding to the general formula (III).

In the general formula (II) of the carboxylic acids, R may also represent a carbocyclic radical which is saturated or contains 1 or 2 unsaturations in the ring, generally having 3 to 7 carbon atoms, preferably 6 carbon atoms in the ring, said ring may be substituted by 1 to 5 $R_1$ radicals, preferably 1 to 3, R1 having the meanings given above for the substituents of the aromatic hydrocarbon radical corresponding to the general formula (III).

Preferred examples of radicals R include the cyclohexyl or cyclohexenyl radicals, optionally substituted by linear or branched alkyl radicals having 1 to 4 carbon atoms.

As mentioned above, R may represent a linear or branched, saturated or unsaturated acyclic aliphatic radical.

More specifically, R represents a linear or branched acyclic aliphatic radical having preferably 1 to 12 carbon atoms, which may be saturated or contains one to several unsaturations on the chain, generally 1 to 3 unsaturations which may be simple or conjugated double bonds or triple bonds.

The hydrocarbon chain may optionally be:
interrupted by one of the following groups:

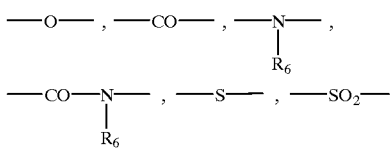

in these formulae $R_6$ represents hydrogen or a linear or branched alkyl radical having 1 to 4 carbon atoms, preferably a methyl or ethyl radical, and/or bearing one of the following substituents:
—OH, —$COOR_5$, —CHO—, —$NO_2$, —CN, —$NH_2$, —SH, —X, —$CF_3$ in these formulae, $R_5$ having the meaning given above.

In a preferred embodiment of the invention, R corresponds to the following formula:

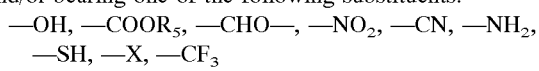

(IV)

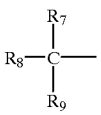

in which $R_7$, $R_8$ and $R_9$, which may be the same or different, are chosen from a hydrogen atom, a linear or branched alkyl radical containing 1 to 10 carbon atoms, a linear or branched alkenyl radical containing 1 to 10 carbon atoms, a linear or branched alkoxy radical containing 1 to 10 carbon atoms, a hydroxyl group, an amine function or a halogen atom or a —$CF_3$ group.

Preferably, $R_7$ and/or $R_8$ and/or $R_9$ represent an unsaturated group.

Even more preferably, in formula (IV), one of the 3 groups $R_7$, $R_8$ and $R_9$ possesses a conjugated double bond with the carbonyl group of the carboxylic acid, ester or anhydride.

It is also possible use a carboxylic acid or derivative corresponding to formula (II) in which R represents a linear or branched, saturated or unsaturated acyclic aliphatic radical which may optionally bear a cyclic substituent. The term ring means a saturated, unsaturated or aromatic, carbocyclic or heterocyclic ring.

The acyclic aliphatic radical may be linked to the ring by a valency bond or by one of the following groups:

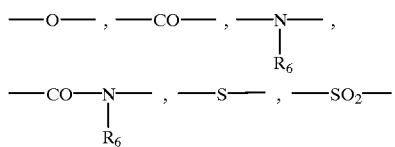

in these formulae, $R_6$ having the meaning given above.

Examples of cyclic substituents that may be envisaged include aromatic or heterocyclic cycloaliphatic substituents, particularly cycloaliphatic substituents containing 6 carbon atoms in the ring or benzene rings, said cyclic substituents themselves optionally bearing 1, 2, 3, 4 or 5 radicals $R_1$, which may be the same or different, $R_1$ having the meanings given above for the substituents of the aromatic hydrocarbon radical corresponding to the general formula (III).

Examples of such radicals include, amongst others, the benzyl radical

In the general formula (II) of carboxylic acids, R may also represent a heterocyclic radical, saturated or unsaturated, containing in particular 5 or 6 atoms in the ring including 1 or 2 heteroatoms such as nitrogen, sulphur and oxygen atoms; the carbon atoms of the heterocycle may optionally be substituted wholly or only partially by radicals $R_1$, $R_1$ having the meanings given above for the substituents of the aromatic hydrocarbon radical corresponding to the general formula (III).

R may also represent a polycyclic heterocyclic radical defined as being either a radical composed of at least 2 aromatic or non-aromatic heterocycles containing at least one heteroatom in each ring and forming ortho- or ortho- and peri-condensed systems, or a radical composed of at least one aromatic or non-aromatic hydrocarbon ring and at least one aromatic or non-aromatic heterocycle forming ortho- or ortho-and peri-condensed systems; the carbon atoms of said rings may optionally be substituted wholly or only partially by radicals $R_1$, $R_1$ having the meanings given above for the substituents of the aromatic hydrocarbon radical corresponding to the general formula (III).

Examples of R groups of the heterocyclic type include, amongst others, furyl, pyrrolyl, thienyl, isoxazolyl, furazanyl, isothiazolyl, imidazolyl, pyrazolyl, pyridyl, pyridazinyl, pyrimidinyl radicals, and quinolyl, naphthyridinyl, benzofuranyl, indolyl radicals.

Examples of carboxylic acids containing at least one carboxylic group corresponding to the formula (II) that may be used include, more particularly, the following carboxylic acids:

saturated aliphatic monocarboxylic acids such as formic, acetic, propionic, butyric, isobutyric, valeric, isovaleric, pivalic, lauric, myristic, palmitic, stearic acids, saturated aliphatic dicarboxylic acids such as oxalic, malonic, succinic, glutaric, adipic, pimelic, suberic, azelaic, sebacic acids, unsaturated aliphatic monocarboxylic or dicarboxylic acids such as acrylic, propiolic, methacrylic, crotonic, isocrotonic, senecloic acid, tiglic, oleic, maleic, fumaric, citraconic, mesaconic acids, saturated or unsaturated carbocyclic carboxylic acids such as camphoric acid, chyrsanthemic acid, heterocyclic carboxylic acids such as furan carboxylic, thiophene carboxylic, pyrrole carboxylic, pyrazine carboxylic acids, nicotinic, isonicotinic, picolinic acid, aromatic carbocyclic carboxylic acids such as benzoic, phthalic, isophthalic, terephthalic acid, naphthalene carboxylic acids, toluic acids, saturated arylaliphatic carboxylic acids such as, in particular, the arylpropionic acids such as 2-phenylpropionic acid, 2-[4-(2-butyl-2) phenyl] propionic acid, 2-(3-benzoylphenyl)propionic acid, 2-(6-methoxy-2-naphthyl)propionic acid or unsaturated acids such as, for example, 2-phenylpropenoic acid, cinnamic acid, halogenated aliphatic or aromatic carboxylic acids such as monofluoroacetic, difluoroacetic, monochloroacetic, dichloroacetic, trichloroacetic, monochloropropionic, α-bromopropionic, α-bromobutyric, trifluoroacetic acid, monofluoro-o-benzoic acid, monofluoro-m-benzoic acid, monofluoro-p-benzoic acid, 2,3-difluorobenzoic acid, 2,4-difluorobenzoic acid, 2,5-difluorobenzoic acid, 3,4-difluorobenzoic acid, 2,3,6-trifluorobenzoic acid, 2,4,5-trifluorobenzoic acid, 2,3,4,5-tetrafluorobenzoic acid, pentafluorobenzoic acid, α,α,α-trifluoro-o-toluic acid, α,α,α-trifluoro-m-toluic acid, α,α,α-trifluoro-p-toluic acid, monochloro-o-benzoic acid, monochloro-m-benzoic acid, monochloro-p-benzoic acid, 2,3-dichlorobenzoic acid, 2,4-dichlorobenzoic acid, 2,5-dichlorobenzoic acid, 2,6-dichlorobenzoic acid, 3,4-dichlorobenzoic acid, 3,5-dichlorobenzoic acid, 2,3,5-trichlorobenzoic acid, 2,3,6-trichlorobenzoic acid, 2-chloro-4,5-difluorobenzoic acid, 3-chloro-2,4,5-trifluorobenzoic acid, monobromo-o-benzoic acid, monobromo-m-benzoic acid, monobromo-p-benzoic acid.

aliphatic, cycloaliphatic arylaliphatic hydroxy acids such as glycollic acid, lactic acid, glyceric acid, 2-hydroxybutanoic acid, 3-hydroxybutanoic acid, 2-methyllactic acid, 2-hydroxy-4-methylthiobutanoic acid, tartronic acid, malic acid, tartaric acid, 1-hydroxycyclopropane carboxylic acid, 2-hydroxyphenylpropanoic acid, 2-hydroxycinnamic acid, 3-hydroxycinnamic acid, 4-hydroxycinnamic acid, the following hydroxybenzoic acids: 2-hydroxybenzoic acid (salicylic acid), 3-hydroxybenzoic acid, 4-hydroxybenzoic acid, 3-methylsalicyclic acid, 4-methylsalicyclic acid, 5-methylsalicylic acid, 3-hydroxy-4-methylbenzoic acid, 3-methoxysalicyclic acid, 4-methoxysalicylic acid, 5-methoxysalicyclic acid, 3-hydroxy-4-methoxybenzoic acid (isovanillic acid), 4-hydroxy-3-methoxybenzoic acid (vanillic acid), 3-hydroxy-4,5-dimethoxybenzoic acid, 4-hydroxy-3,5-dimethoxybenzoic acid (syringic acid), 5-hydroxyisophthalic acid, 3-aminosalicylic acid, 4-aminosalicylic acid, 5-aminosalicylic acid, 3-hydroxy-2-aminobenzoic acid, 3-nitrosalicylic acid, 3-hydroxy-4-nitrobenzoic acid, 4-hydroxy-3-nitrobenzoic acid, 3-hydroxy-4-methyl-2-nitrobenzoic acid, 3,5-diiodosalicylic acid, 2,3-dihydroxybenzoic acid, 2,4-dihydroxybenzoic acid, 2,5-dihydroxybenzoic acid, 2,6-dihydroxybenzoic acid, 3,4-dihydroxybenzoic acid (protocatechuic acid), 3,5-dihydroxybenzoic acid, 3,5-dihydroxy-4-methylbenzoic acid, 2,3,4-trihydroxybenzoic acid, 2,4,6-trihydroxybenzoic acid, 3,4,5-trihydroxybenzoic acid, the alkoxy and phenoxy acids such as methoxyacetic, phenoxyacetic, 2,4-dichlorophenoxyacetic, phenoxypropionic, 2,4-dichlorophenoxypropionic, p-hydroxyphenoxypropionic, m-chlorophenoxypropionic acid, 4-phenoxybenzoic acid, (4-carboxy-4-phenoxy)benzoic acid, piperonylic acid, the oxo acids such as 2-acetylbenzoic acid, 4-acetylbenzoic acid, 2-benzoylbenzoic acid, 4-benzoylbenzoic acid, the acyloxy acids such as 3-benzoyloxypropionic acid, 2-acetoxybenzoic acid, 4-acetoxybenzoic acid, the amido acids such as 2-acetamidoacrylic acid, 2-acetamidobenzoic acid, 3-acetamidobenzoic acid, 4-acetamidobenzoic acid, amino acids possibly N protected by a protective group such as, for example, the following groups: acyl (acetyl, benzoyl), BOC (butyloxycarbonyl), CBZ (carbobenzoxy), FMOC (fluorenyl-9 methoxycarbonyl), MSOC (methanesulphenyl-2-ethoxycarbonyl).

The following amino acids may be mentioned:

aliphatic amino acids: glycine, alanine, valine, leucine, isoleucine, hydroxylated amino acids: serine, threonine, amino acids containing sulphur: cysteine, methionine, dicarboxylic amino acids and amides thereof aspartic acid, asparagine, glutamic acid, glutamine, amino acids having two basic groups: lysine, arginine, histidine, aromatic amino acids: phenylalanine, tyrosine, tryptophan, imino acids: proline, hydroxyproline.

The acids used in preference are, more particularly, carboxylic acids such as benzoic acid, 3,4-difluorobenzoic acid, 4-chlorobenzoic acid, 4-trifluoromethylbenzoic acid, salicylic acid, 3-hydroxybenzoic acid, 4-hydroxybenzoic acid, vanillic acid, 3,4-dimethoxybenzoic acid, 4-methoxybenzoic acid, 3,4-dioxymethylenebenzoic acid, cinnamic acid, 6-methoxy-2-naphthalene carboxylic acid, 6-hydroxy-2-naphthalene carboxylic acid, acetic acid, trifluoroacetic acid, 2-methylbutyric acid, saturated or unsaturated aliphatic fatty acids having 6 to 20 carbon atoms, preferably heptanoic acid, nonanoic acid, undecanoic acid, oleic acid, heptadecanoic acid, stearic acid, lauric acid, undecenoic acid, 2-methylnonanoic acid, 3,7-dimethyl-2,6-octadiene carboxylic acid, senecioic acid, cyclohexanoic acid.

In accordance with the present invention, a carboxylic acid may be used in the form of its anhydride.

Examples of carboxylic anhydrides include more particularly anhydrides of the carboxylic acids mentioned above and cyclic anhydrides.

Indeed, if the anhydride corresponds to the formula (II) in which R' is an

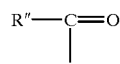

group the two groups R" and R" may be linked together to form a saturated or unsaturated ring having 5 to 7 atoms containing the anhydride function. They form preferably a linear or branched alkylene radical having 2 to 6 carbon atoms and even more preferably a radical —(CH$_2$)$_t$— where t is equal to 2 to 4.

Examples of such cyclic anhydrides include succinic anhydride or maleic anhydride.

If the anhydride corresponds to the formula (II) in which R' is an

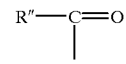

group, the two groups R and R", by way of two vicinal atoms, may together form a bridge of an orthocondensed bicyclic system.

The preferred compounds are bicyclic and are composed of a benzene ring and of a heterocycle since the ring contains the oxygen atom of the anhydride function, said ring preferably having 5 to 6 atoms. Examples of such cyclic anhydrides of polycarboxylic acids include phthalic anhydride.

The process of the invention is used in the gaseous phase.

Advantageously, the reaction is carried out at a temperature between 100° C. and 500° C. and even more preferably at between 200 and 400° C. It is understood that the temperature is adjusted by the man skilled in the art depending on the starting acid, and the required rate of reaction.

Moreover, it may be particularly advantageous to activate the catalyst beforehand by means of a very high temperature. In particular, the catalyst may be subjected to temperatures close to about 500° C. beforehand, and preferably 450° C. Activation is advantageously carried out under a stream of hydrogen.

A practical way of implementing the present invention consists in introducing into a reactor a desired quantity of catalyst, optionally between 2 beds of quartz, in order to promote the contacting of the reagents. The temperature of the reactor is then raised under a stream of hydrogen to a determined value, making it possible to activate the catalyst, then brought back to the reaction temperature. The acid is then injected at the desired flow rate and the aldehyde formed is recovered.

In preference, the acid is injected directly in the gaseous form after having been vaporised by heating.

However, it may also be injected in solution in an inert solvent for the reaction. Inert solvents include in particular aliphatic hydrocarbons (for example, hexane), alicyclic hydrocarbons (for example, cyclohexane), aromatic hydrocarbons (for example, toluene), or ethers (for example, dimethoxyethane).

Under the effect of the high temperature, the acid thus injected is vaporised in the first bed of quartz. The hydrogen may be injected at atmospheric pressure or under a slight pressure compatible with the vapour phase (a few bars, for example 0.5 to 10 bar). The hydrogen may also be diluted in an inert gas such as nitrogen or helium.

Advantageously, the hydrogen is injected at a flow rate of between 0.1 and 10 litres per hour per 1 ml of catalyst, and the acid at a liquid flow rate at most equal to 10 ml/h, and preferably between 0.5 and 5 ml/h.

At the end of the reaction, the aldehyde is recovered by any suitable means such as distillation or crystallisation. In certain cases, particularly in the case of fluoral, the aldehyde may be obtained in the hydrated form.

The catalyst obtained according to the process of the invention may be used in a process for the preparation of numerous aldehydes which are used as pharmaceutical and/or agrochemical intermediates such as, for example, 3,4-difluorobenzaldehyde, 4-chlorobenzaldehyde.

It is particularly interesting for the preparation of salicylic aldehyde which may be used, inter alia, for the preparation of coumarine: the latter resulting from a well known cyclisation stage and widely described in the literature (KIRK-OTHMER—Encyclopedia of Chemical Technology 7, p. 198, 3rd edition).

The catalyst obtained according to the invention is also suitable for the preparation of other aromatic aldehydes such as 3-hydroxybenzaldeyde, 4-hydroxybenzaldehyde, vanillin, veratraldehyde, p-anisaldehyde, piperonal, cinnamic aldehyde.

The present invention may also be used for the synthesis of various aldehydes. It may be used to prepare saturated aldehydes such as fluoral or acetaldehyde. It is particularly suitable for the synthesis of unsaturated aldehydes, particularly in terpene chemistry (prenal, citral etc.), intermediates in the synthesis of vitamins A or E.

It will not be beyond the scope of the present invention to produce, according to the process of the invention, aldehydes in the form of their derivatives such as their acetals or their hemiacetals, by reaction of the aldehyde and an alcohol which is introduced either at the same time as the acid or at the end of the reaction. Examples of alcohols conventionally used include methanol or ethanol.

Embodiments of the invention are given below by way of illustration without limiting its scope.

EXAMPLE 1

Preparation of the Catalyst Impregnated in the Dry State 1.92 g of $RuCl_3 \cdot xH_2O$ containing 42% by weight of ruthenium, and 10.7 g of $SnCl_2$, $2H_2O$ and 13 ml of an aqueous solution of 3N hydrochloric acid are introduced into a Woulfe bottle.

The mixture is heated to 90° C. with stirring.

The solution is kept at this temperature for 1 hour.

This solution is then cooled.

40 g of beads of alumina α are impregnated (specific surface=5–10 $m^2/g$ and pore volume=44–54 $cm^3$ per 100 g) sold by Rhône Poulenc under the name Spheralite 512, the diameter of the beads being 2 to 4 mm.

The impregnated beads are then dried in a ventilated oven until a constant weight is obtained.

The catalyst is then treated at 450° C. under a stream of hydrogen for 4 hours.

EXAMPLE 2

Preparation of the Catalyst From a Support in the Form of a Powder 1.92 g of $RuCl_3 \cdot xH_2O$ containing 42% by weight of ruthenium, and 10.7 g of $SnCl_2$, $2H_2O$ and 13 ml of an aqueous solution of 3N hydrochloric acid are introduced into a Woulfe bottle.

The mixture is heated to 90° C. for 1 hour with stirring.

This solution is then cooled to 20° C.

80 g of silica Degussa OX50 (specific surface=50 $m^2/g$, average size of primary particles 40 nm) and 4000 ml of water are then added.

The precipitated is filtered and washed with water.

The cake is then mixed and extruded.

The extrudates are then dried in the air until a constant weight is obtained.

The catalyst is then treated with hydrogen at 450° C. under a stream of hydrogen for 4 hours.

EXAMPLE 3

Hydrogenation of Trifluoroacetic Acid 60 g of catalyst prepared according to Example 1 are introduced into a tubular nickel reactor with a diameter of 2.54 cm.

The said catalyst is treated under a stream of hydrogen of 11 litres per hour whilst heating to 450° C.

These conditions are maintained for 15 hours.

The temperature is reduced to 320° C. and trifluoroacetic acid is injected in a quantity of 20 g/h.

The rate of conversion is 80% and the fluoral hydrate yield is 70%.

After 300 hours, the performances of the catalyst are identical.

What is claimed is:

1. A process for the preparation of a bimetallic ruthenium/tin catalyst, comprising a support and a metallic phase covering at least in part said support, said catalyst containing at least in part a ruthenium-tin intermetallic phase at least partially in the form of a compound of formula $Ru_3Sn_7$, said process comprising the step of:

a) carrying out a reduction of a complex of ruthenium having an electrovalency of −4 and a coordination number of 6, wherein at least one of the ligands being a tin halide, the other ligands optionally being a halogen atom.

2. A process according to claim 1, wherein the complex corresponds to the following formula (A):

$$[Ru(SnX_3)_{6-n}X_n]^{4-} \quad (A)$$

wherein: X represents a halogen atom, and n is a number from 0 to 2.

3. A process according to claim 2, wherein X represents an atom of chlorine or bromine, and n is equal to 1.

4. A process according to claim 2, wherein the complex corresponds to one of the following formulas (A):

$[Ru(SnCl_3)_6]^{4-}$ $[Ru(SnCl_3)_5Cl]^{4-}$, or $[Ru(SnCl_3)_4Cl_2]^{4-}$.

5. A process according to claim 1, wherein the complex of ruthenium is a ruthenium halide and the reduction is carried out in the presence of an acid.

6. A process according to claim 5, wherein the ruthenium halide is a ruthenium III halide in the anhydrous or hydrated form, and the tin halide is in the anhydrous or hydrated form.

7. A process according to claim 6, wherein the ruthenium halide is a ruthenium III chloride, the tin halide is tin II chloride, and the acid is hydrochloric acid.

8. A process according to claim 6, wherein the ratio between the number of moles of ruthenium halide and the number of moles of tin halide is between 0.10 and 0.5.

9. A process according to claim 6, wherein the acid is a hydracid whose halide is identical to the halide used in the ruthenium halide and tin halide.

10. A process according to claim 6, wherein the quantity of acid used is at least 1 mole of acid per mole of ruthenium halide.

11. A process according to claim 10, wherein the quantity of acid used is between 1 and 5 moles of acid per mole of ruthenium halide.

12. A process according to claim 11, wherein the quantity of acid used is of about 3 moles of acid per mole of ruthenium halide.

13. A process according to claim 9, further comprising the step of:

b) mixing, in any order, the ruthenium halide, the tin halide and the strong acid to obtain a reaction mixture.

14. A process according to claim 13, further comprising the step of:

c) raising the temperature of the reaction mixture to a temperature from 20° C. to 100° C.

15. A process according to claim 14, wherein in step c), the temperature of the reaction mixture is raised to a temperature from 70° C. to 90° C.

16. A process according to claim 14, further comprising the steps of:
   d) restoring the temperature of the reaction mixture to ambient temperature to obtain an aqueous solution of the complex,
   e) hydrolyzing the complex by adding water, and
   f) separating the precipitated bimetallic ruthenium/tin catalyst so obtained.

17. A process according to claim 16, further comprising the steps of:
   before step e), adding the support in the form of a powder to said reaction mixture, and
   after step f), mixing and extruding the bimetallic ruthenium/tin catalyst with said powder to obtained the formed catalyst.

18. A process according to claim 16, wherein, the quantity of water used in the hydrolyzing step e) represents 1 to 100 times the weight of the complex.

19. A process according to claim 16, further comprising the step of:
   g) impregnating the support with the aqueous solution of the complex obtained in step d).

20. A process according to claim 19, wherein the support is in the form of a powder, beads, granules, or extrudates.

21. A process according to claim 19, wherein the support is a metal oxide, a zirconium oxide, an active carbon, or a resin.

22. A process according to claim 19, wherein the ruthenium content of the supported catalyst is between 0.1 and 20.0% by weight.

23. A process according to claim 19, wherein the solution of the complex contains the ruthenium and tin complex in a quantity of 1% to 20% by weight of ruthenium.

24. A process according to claim 19, wherein step g) comprises impregnating the support by spraying the aqueous solution containing the ruthenium and tin complex onto the support brought into motion by the rotation of a rotatable outer ring.

25. A process according to claim 19, wherein step g) comprises the impregnation of the support by immersion into the aqueous solution of the said complex.

26. A process according to claim 19, wherein step g) comprises impregnation of the support "in the dry state" with the aqueous solution containing the ruthenium and tin complex.

27. A process according to claim 19, further comprising the step of:
   h) drying the impregnated support in the air at a temperature ranging from ambient temperature to 100° C.

28. A process according to claim 1, wherein the reduction of said complex is carried out by bringing it into contact with hydrogen.

29. A process according to claim 28, wherein the hydrogen is injected at atmospheric pressure or under a pressure from 0.5 to 10 bar, and is optionally diluted in an inert gas.

30. A process according to claim 28, wherein the reduction reaction is carried out at a temperature of at least 350° C.

31. A process according to claim 30, wherein the reduction reaction is carried out at a temperature of between 350 and 600° C.

32. A process according to claim 29, wherein the reduction reaction is carried out during the use of the catalyst.

33. A process according to claim 1, wherein the intermetallic phase has an atomic ratio Sn/Ru at least equal to 2/3.

34. A process according to claim 33, wherein the phase containing the ruthenium and the tin has an atomic ratio Sn/Ru at most equal to 3.

35. A process according to claim 33, wherein the metallic phase contains at least 50% of said intermetallic phase.

36. A process according to claim 35, wherein at least 90% of the ruthenium present on the support is in the form of said catalytic phase covering said support.

37. A method of use of a catalyst produced by a process according to claim 1, in a process for the preparation of aldehydes and derivatives thereof by reduction by hydrogen, in the presence of said catalyst, in the vapor phase, of carboxylic acids, esters or anhydrides.

38. A method of use of the catalyst according to claim 37, for the preparation of aldehydes having the general formula:

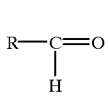

(I)

in which R represents a hydrogen atom or an optionally substituted hydrocarbon radical containing 1 to 40 carbon atoms which may be a saturated or unsaturated, linear or branched, acyclic aliphatic radical; a saturated, unsaturated or aromatic, monocyclic or polycyclic, carbocyclic or heterocyclic radical, by reduction of esters, anhydrides or acids having the formula:

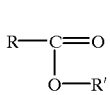

(II)

in which:
   R is defined as above,
   R' represents:
      a R group as defined above,
      a

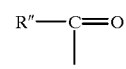

group in which R" has the meaning given for R,
   the two groups R and R" being optionally linked to form a saturated or unsaturated ring having 5 to 7 atoms and containing the anhydride function, or
   the two groups R and R", by way of two vicinal atoms, optionally forming a bridge of an ortho-condensed bicyclic system.

39. A method of use of a catalyst according to claim 38, wherein the carboxylic acid or derivative thereof corresponding to the general formula (II) is:
   a saturated aliphatic monocarboxylic acid,
   a saturated aliphatic dicarboxylic acid,
   an unsaturated aliphatic monocarboxylic or dicarboxylic acid,
   a saturated or unsaturated carbocyclic carboxylic acid,
   a heterocyclic carboxylic acid,
   an aromatic carbocyclic carboxylic acid,
   a saturated or unsaturated arylaliphatic carboxylic acid,
   a halogenated aliphatic or aromatic carboxylic acid,
   a aliphatic, cycloaliphatic, arylaliphatic hydroxy acid,
   a hydroxybenzoic acid,
   an alkoxy and phenoxy acid,
   an oxo acid, an acyloxy acid, an amido acid, or an optionally N-protected amino acid.

40. A method of use of the catalyst according to claim 39, wherein the carboxylic acid or derivative thereof is selected from the group consisting of benzoic acid, 3,4-difluorobenzoic acid, 4-chlorobenzoic acid, 4-trifluoromethylbenzoic acid, salicylic acid, 3-hydroxybenzoic acid, 4-hydroxybenzoic acid, vanillic acid, 3,4-dimethoxybenzoic acid, 4-methoxybenzoic acid, 3,4-dioxymethylenebenzoic acid, cinnamic acid, 6-methoxy-2-naphthalene carboxylic acid, 6-hydroxy-2-naphthalene carboxylic acid, acetic acid, trifluoroacetic acid, 2-methylbutyric acid, heptanoic acid, nonanoic acid, undecanoic acid, oleic acid, heptadecanoic acid, stearic acid, lauric acid, undecenoic acid, 2-methylnonanoic acid, 3,7-dimethyl-2,6-octadiene carboxylic acid, senecioic acid, and cyclohexanoic acid.

* * * * *